US011607118B2

(12) United States Patent
Hong

(10) Patent No.: US 11,607,118 B2
(45) Date of Patent: Mar. 21, 2023

(54) FLUID SUPPLY DEVICE FOR ENDOSCOPE

(71) Applicant: Chang Gul Hong, Seongnam-si (KR)

(72) Inventor: Chang Gul Hong, Seongnam-si (KR)

( * ) Notice: Subject to any disclaimer, the term of this patent is extended or adjusted under 35 U.S.C. 154(b) by 212 days.

(21) Appl. No.: 15/930,200

(22) Filed: May 12, 2020

(65) Prior Publication Data

US 2021/0052148 A1    Feb. 25, 2021

(30) Foreign Application Priority Data

Aug. 23, 2019 (KR) .......................... 10-2019-0103923
Mar. 31, 2020 (KR) .......................... 10-2020-0039056

(51) Int. Cl.
*A61B 1/015* (2006.01)
*A61B 1/00* (2006.01)

(52) U.S. Cl.
CPC .......... *A61B 1/015* (2013.01); *A61B 1/00042* (2022.02); *A61B 1/00045* (2013.01); *A61B 1/00068* (2013.01); *A61B 1/00119* (2013.01)

(58) Field of Classification Search
CPC ......... A61B 1/123; A61B 1/125; A61B 1/126; A61B 1/0045; A61B 1/00068; A61B 1/00119
See application file for complete search history.

(56) References Cited

U.S. PATENT DOCUMENTS

| | | | | |
|---|---|---|---|---|
| 4,276,023 A * | 6/1981 | Phillips | ................. | A61C 1/0061 604/24 |
| 4,800,869 A * | 1/1989 | Nakajima | .......... | A61B 1/00068 600/158 |
| 4,971,034 A * | 11/1990 | Doi | .......................... | A61M 1/74 600/560 |
| 5,191,878 A * | 3/1993 | Iida | ..................... | A61B 1/00091 600/157 |
| 5,386,817 A * | 2/1995 | Jones | ................. | A61B 1/00135 600/125 |
| 5,613,954 A * | 3/1997 | Nelson | ............... | A61B 17/3421 604/167.03 |
| 5,800,383 A * | 9/1998 | Chandler | ............... | A61M 31/00 604/35 |
| 5,879,288 A * | 3/1999 | Suzuki | ............... | A61B 1/00124 600/176 |
| 6,334,844 B1 * | 1/2002 | Akiba | ................. | A61B 1/00068 600/156 |
| 6,595,957 B1 * | 7/2003 | Griffiths | .............. | A61M 3/0212 604/20 |

(Continued)

FOREIGN PATENT DOCUMENTS

WO    WO-2005110203 A1 *  11/2005  ............... A61B 1/12

*Primary Examiner* — John P Leubecker
*Assistant Examiner* — Jae Woo
(74) *Attorney, Agent, or Firm* — STIP Law Group, LLC

(57) ABSTRACT

The present invention relates to a fluid supply device for an endoscope, including: a liquid supply unit for supplying liquids to the endoscope; a gas supply unit for supplying gases to the endoscope; and a control unit for controlling operations of the liquid supply unit and the gas supply unit, wherein the control unit includes: a foot switch located on the floor of an operating room to receive control commands on the operations of the liquid supply unit and the gas supply unit from a surgeon who uses the endoscope; and a controller for selectively operating the liquid supply unit and the gas supply unit according to the control commands received.

3 Claims, 9 Drawing Sheets

(56) References Cited

U.S. PATENT DOCUMENTS

| | | | | |
|---|---|---|---|---|
| 8,221,313 B2* | 7/2012 | Noda | A61B 1/015 | 600/156 |
| 8,298,494 B2* | 10/2012 | Komiya | A61B 1/125 | 422/292 |
| 8,535,219 B2* | 9/2013 | Smith | A61B 1/00071 | 600/179 |
| 8,591,464 B2* | 11/2013 | Kumar | A61M 3/0212 | 604/246 |
| 8,979,788 B2* | 3/2015 | Demers | A61M 1/3666 | 604/4.01 |
| 9,474,848 B2* | 10/2016 | Williams | A61M 3/0258 | |
| 9,724,481 B2* | 8/2017 | Kasuya | A61M 13/003 | |
| 2001/0039370 A1* | 11/2001 | Takahashi | A61B 1/015 | 600/159 |
| 2004/0030367 A1* | 2/2004 | Yamaki | A61B 90/00 | 607/60 |
| 2005/0159702 A1* | 7/2005 | Sekiguchi | A61B 1/00082 | 604/99.01 |
| 2005/0217727 A1* | 10/2005 | Uesugi | A61M 13/003 | 137/315.01 |
| 2005/0222535 A1* | 10/2005 | Uesugi | A61B 1/015 | 600/560 |
| 2006/0030751 A1* | 2/2006 | Uesugi | A61B 1/00068 | 600/101 |
| 2006/0100485 A1* | 5/2006 | Arai | A61B 1/00068 | 600/101 |
| 2006/0106285 A1* | 5/2006 | Boulais | A61B 1/128 | 600/156 |
| 2006/0135851 A1* | 6/2006 | Yamazaki | A61B 1/00137 | 600/156 |
| 2006/0266423 A1* | 11/2006 | Akiba | A61B 1/125 | 137/565.01 |
| 2007/0043262 A1* | 2/2007 | Levy | A61B 1/00068 | 600/156 |
| 2007/0107152 A1* | 5/2007 | Noguchi | A61B 1/125 | 15/104.095 |
| 2007/0179341 A1* | 8/2007 | Okada | A61B 1/00137 | 600/156 |
| 2007/0225566 A1* | 9/2007 | Kawanishi | A61B 1/00091 | 600/157 |
| 2007/0232853 A1* | 10/2007 | Yamaya | A61B 1/00042 | 600/116 |
| 2007/0238929 A1* | 10/2007 | Aizenfeld | A61B 1/015 | 600/158 |
| 2007/0244363 A1* | 10/2007 | Sano | A61B 1/015 | 600/118 |
| 2008/0294008 A1* | 11/2008 | Toyama | A61B 1/015 | 600/156 |
| 2008/0317648 A1* | 12/2008 | Miyako | A61B 90/70 | 422/300 |
| 2009/0020142 A1* | 1/2009 | Miyako | A61B 1/123 | 134/22.14 |
| 2009/0023996 A1* | 1/2009 | Fujikura | A61M 25/10188 | 600/115 |
| 2009/0044845 A1* | 2/2009 | Cui | A61B 1/123 | 134/201 |
| 2009/0062611 A1* | 3/2009 | Toyama | A61B 1/015 | 600/118 |
| 2009/0220377 A1* | 9/2009 | Hasegawa | A61B 1/123 | 422/292 |
| 2009/0287093 A1* | 11/2009 | Ferren | A61B 5/026 | 600/529 |
| 2009/0287101 A1* | 11/2009 | Ferren | A61B 5/026 | 600/504 |
| 2010/0022834 A1* | 1/2010 | Noda | A61B 1/015 | 600/118 |
| 2012/0016293 A1* | 1/2012 | Hayashi | A61B 1/126 | 604/24 |
| 2012/0031506 A1* | 2/2012 | Komiya | A61B 1/125 | 137/237 |
| 2012/0289910 A1* | 11/2012 | Shtul | A61M 3/0241 | 604/266 |
| 2014/0066839 A1* | 3/2014 | Torisawa | A61M 13/003 | 604/26 |
| 2014/0371667 A1* | 12/2014 | Kasuya | A61B 1/3132 | 604/26 |
| 2015/0073364 A1* | 3/2015 | Cheng | A61M 1/74 | 604/319 |
| 2015/0080757 A1* | 3/2015 | Torisawa | A61B 1/015 | 600/560 |
| 2015/0265784 A1* | 9/2015 | Lampert | A61B 1/00006 | 604/26 |
| 2016/0106934 A1* | 4/2016 | Hiraga | A61B 1/3132 | 604/26 |
| 2016/0184524 A1* | 6/2016 | Fech | A61M 5/1407 | 604/500 |
| 2018/0056664 A1* | 3/2018 | Koike | B41J 2/17509 | |
| 2018/0221598 A1* | 8/2018 | Silver | A61M 13/006 | |
| 2019/0076009 A1* | 3/2019 | Yang | A61L 2/24 | |
| 2019/0125912 A1* | 5/2019 | Bommarito | A61L 2/26 | |
| 2021/0060495 A1* | 3/2021 | Bérubé | B01D 65/02 | |
| 2021/0076913 A1* | 3/2021 | Yamanashi | A61B 1/00089 | |
| 2021/0186469 A1* | 6/2021 | Johnsen | A61B 10/04 | |

* cited by examiner

FLUID SUPPLY DEVICE FOR ENDOSCOPE

CROSS REFERENCE TO RELATED APPLICATION OF THE INVENTION

The present application claims the benefit of Korean Patent Applications Nos. 10-2019-0103923 filed in the Korean Intellectual Property Office on Aug. 23, 2019 and 10-2020-0039056 filed in the Korean Intellectual Property Office on Mar. 31, 2020 the entire contents of which are incorporated herein by reference.

BACKGROUND OF THE INVENTION

Field of the Invention

The present invention relates to a fluid supply device for an endoscope, and more particularly, to a fluid supply device for an endoscope that is capable of allowing a surgeon to easily control supply of water, a bubble remover, and air to the endoscope, without any surgical assistant's help.

Background of the Related Art

An endoscope is an instrument with a light and camera inserted into a patient's body to view whether the body is normal or not, and if necessary, a simple surgery may be carried out through the endoscope. As it is convenient to use the endoscope and the examination result through the endoscope is accurate, today, the endoscope has been widely used in medical fields.

During the use of the endoscope, further, some kinds of fluids are used. For example, a cleaning liquid is injected into the patient's body so as to ensure a surgeon's view field through cleaning, and a bubble remover is needed to remove gas in the intestines. So as to clearly view the patient's body, also, air or water is used to clean or expand the patient's body.

In a conventional practice, by the way, the cleaning liquid or air is injected manually into the patient's body by means of a syringe after a pipe has been inserted into an endoscope channel, so that an additional surgical assistant as well as the surgeon (doctor) has to be needed. However, the need of two or more persons for an endoscopic surgery causes manpower waste, and the surgical assistant's actions are made after the surgeon's commands have issued, thereby making the surgeon feel uncomfortable and extending the total surgery time.

So as to remove such problems, there have been developed endoscopes with various control devices attached to a control panel so as to allow a surgeon to directly control the supply of fluids. In this case, however, the number of devices controllable by the surgeon's fingers is limited so that it is impossible to simultaneously control the devices and erroneous control may occur. Further, it is impossible to freely control the supply speeds of fluids and the amounts of fluids supplied according to the skill level of the surgeon.

If the cleaning liquid or the bubble remover is used, furthermore, the liquid may remain in a supply pipe connected to the endoscope, so that they may be undesirably contaminated or degenerated.

SUMMARY OF THE INVENTION

Accordingly, the present invention has been made in view of the above-mentioned problems occurring in the related art, and it is an object of the present invention to provide a fluid supply device for an endoscope that is capable of allowing a surgeon to easily control the supply of various fluids, the supply speed, and amounts of fluids supplied, without any surgical assistant's help.

It is another object of the present invention to provide a fluid supply device for an endoscope that is capable of utilizing a surgeon's foot in controlling the endoscope, thereby improving a degree of freedom of the surgeon's fingers.

It is yet another object of the present invention to provide a fluid supply device for an endoscope that is capable of preventing a fluid supplied to a patient's body from flowing back thereto after an operation has been stopped.

It is still another object of the present invention to provide a fluid supply device for an endoscope that is capable of removing a liquid remaining in a liquid supply flow path and drying an interior of the liquid supply flow path after the liquid has been supplied thereto.

It is yet still another object of the present invention to provide a fluid supply device for an endoscope that is capable of maintaining a given temperature of a liquid supplied.

To accomplish the above-mentioned objects, according to one aspect of the present invention, there is provided a fluid supply device for an endoscope, including: a liquid supply unit for supplying liquids to the endoscope; a gas supply unit for supplying gases to the endoscope; and a control unit for controlling operations of the liquid supply unit and the gas supply unit, wherein the control unit includes: a foot switch located on the floor of an operating room to receive control commands on the operations of the liquid supply unit and the gas supply unit from a surgeon who uses the endoscope; and a controller for selectively operating the liquid supply unit and the gas supply unit according to the control commands received.

According to the present invention, desirably, the fluid supply device further includes: a liquid supply flow path for connecting the liquid supply unit and the endoscope; a gas supply flow path for connecting the gas supply unit and the endoscope; and a bypass flow path for connecting the liquid supply flow path and the gas supply flow path, wherein if the bypass flow path is open, the gas in the gas supply flow path flows into the liquid supply flow path.

According to the present invention, desirably, the liquid supply unit includes: a first liquid tank for storing the first liquid; a second liquid tank for storing the second liquid; and a liquid pump for selectively supplying the first liquid and the second liquid to the endoscope, and the liquid pump is operated by the control of the controller.

According to the present invention, desirably, the liquid supply unit further includes: a first opening and closing valve located on a flow path connecting the first liquid tank and the liquid pump; a second opening and closing valve located on a flow path connecting the second liquid tank and the liquid pump; and a third opening and closing valve located on a flow path connecting the liquid pump and the endoscope, and the first opening and closing valve, the second opening and closing valve, and the third opening and closing valve are selectively open and closed by the control of the controller.

According to the present invention, desirably, the liquid supply unit further includes a temperature adjustment part for constantly maintaining given temperatures of the first liquid and the second liquid stored in the first liquid tank and the second liquid tank.

According to the present invention, desirably, the gas supply unit includes: a bubble generator for producing bubbles; and a blower for supplying the bubbles produced from the bubble generator to the endoscope, and the bubble generator and the blower are operated by the control of the controller.

According to the present invention, desirably, the gas supply unit includes: a first gas tank for storing the first gas; a second gas tank for storing the second gas; and a gas pump for supplying the first gas and the second gas to the endoscope, and the gas pump is operated by the control of the controller.

According to the present invention, desirably, the gas supply unit further includes: a fourth opening and closing valve located on a flow path connecting the first gas tank and the gas pump; a fifth opening and closing valve located on a flow path connecting the second gas tank and the gas pump; and a sixth opening and closing valve located on a flow path connecting the gas pump and the endoscope, and the fourth opening and closing valve, the fifth opening and closing valve, and the sixth opening and closing valve are selectively open and closed by the control of the controller.

According to the present invention, desirably, the fluid supply device further includes a connecting unit for connecting the liquid supply unit and the gas supply unit to the endoscope, the connecting unit including: a first input terminal for receiving the liquids or the gases from the liquid supply unit or the gas supply unit; a second input terminal having a space formed at an interior thereof to insert a surgical instrument thereinto; and an output terminal whose one end is connected to the first input terminal and the second input terminal and whose other end is connected to the endoscope so as to guide the liquids or the gases supplied from the first input terminal or the surgical instrument inserted into the second input terminal to the endoscope.

According to the present invention, desirably, an angle between the first input terminal and the second input terminal ranges from 30 to 45°.

According to the present invention, desirably, the fluid supply device further includes a Y-shaped connector for connecting the liquid supply unit and the gas supply unit to the first input terminal of the connecting unit.

According to the present invention, desirably, the control unit includes: a first input dial for adjusting the amount of liquid discharged; a second input dial for adjusting the amount of gas discharged; and a display part for transmitting information on operating states of the liquid supply unit and the gas supply unit to the surgeon.

According to the present invention, desirably, the liquid supply unit includes a first backflow prevention valve for preventing the liquid discharged from flowing back, and the gas supply unit includes a second backflow prevention valve for preventing the gas discharged from flowing back.

To accomplish the above-mentioned objects, according to another aspect of the present invention, there is provided a fluid supply device for an endoscope, including: a liquid tank for storing a liquid; a liquid supply flow path for connecting the liquid tank to the endoscope; a liquid pump located on the liquid supply flow path to supply the liquid stored in the liquid tank to the endoscope; a gas tank for storing a gas; a gas supply flow path for connecting the gas tank to the endoscope; a gas pump located on the gas supply flow path to supply the gas stored in the gas tank to the endoscope; a bypass flow path for connecting the liquid supply flow path and the gas supply flow path; a first opening and closing valve located between the liquid tank and the liquid pump on the liquid supply flow path; a second opening and closing valve located between the gas pump and the endoscope on the gas supply flow path; a third opening and closing valve located on the bypass flow path; and a control unit for controlling operations of the liquid pump and the gas pump and the opening and closing operations of the first opening and closing valve, the second opening and closing valve, and the third opening and closing valve.

According to the present invention, desirably, wherein one end of the bypass flow path connected to the liquid supply flow path is connected to the downstream flow under the first opening and closing valve with respect to the liquid tank, and the other end of the bypass flow path connected to the gas supply flow path is connected to the downstream flow under the gas pump and the upstream flow above the second opening and closing valve with respect to the liquid tank.

According to the present invention, desirably, the fluid supply device further includes a suction pump located on the liquid supply flow path to suck the gas stored in the gas tank to the liquid supply flow path through the bypass flow path.

According to the present invention, desirably, the control unit includes: a foot switch located on the floor of an operating room to receive control commands from a surgeon who uses the endoscope; and a controller for controlling operations of the liquid pump, the gas pump, the first opening and closing valve, the second opening and closing valve, and the third opening and closing valve according to the control commands received.

BRIEF DESCRIPTION OF THE DRAWINGS

The above and other objects, features and advantages of the present invention will be apparent from the following detailed description of the embodiments of the invention in conjunction with the accompanying drawings, in which.

DETAILED DESCRIPTION OF THE EMBODIMENTS

Figure 1:
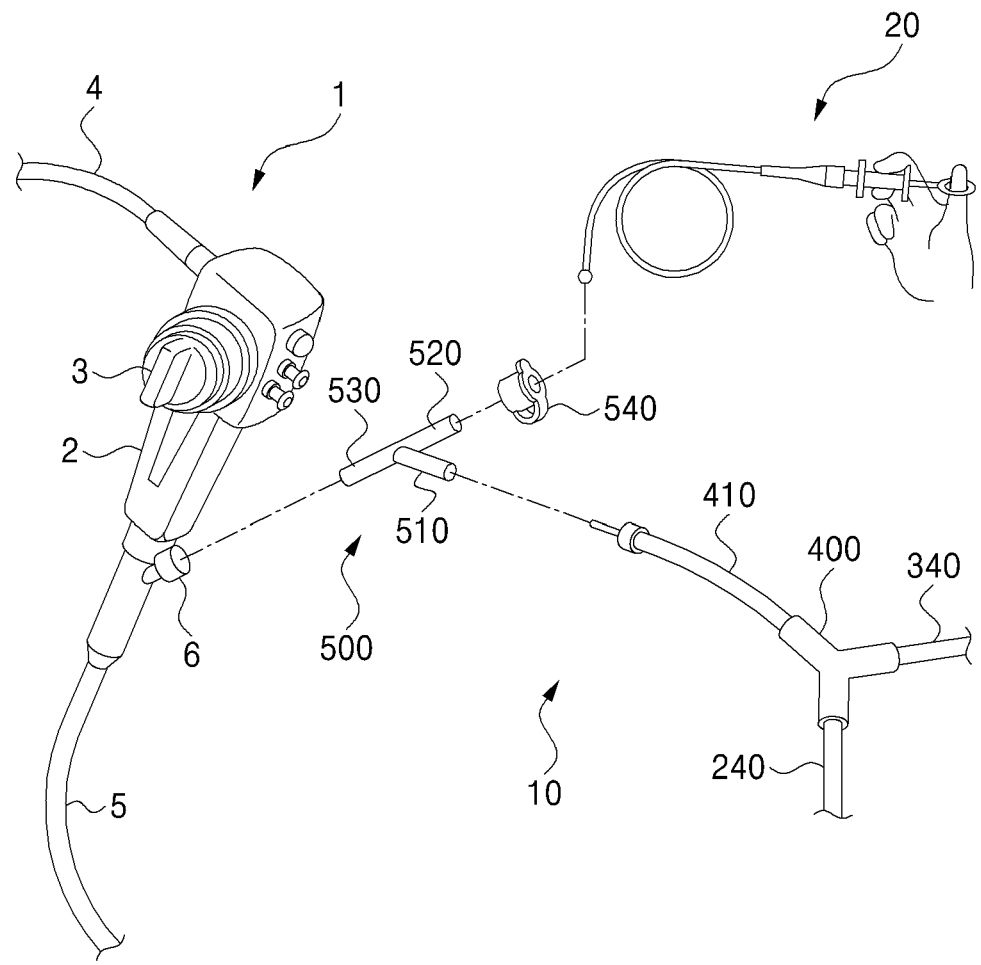
FIG. 1 is a perspective view showing an endoscope.

Before the present invention is disclosed and described, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure.

The present invention may be modified in various ways and may have several exemplary embodiments. Specific exemplary embodiments of the present invention are illustrated in the drawings and described in detail in the detailed description. However, this does not limit the invention within specific embodiments and it should be understood that the invention covers all the modifications, equivalents, and replacements within the idea and technical scope of the invention.

Terms, such as the first, the second, A, and B, may be used to describe various elements, but the elements should not be restricted by the terms. The terms are used to only distinguish one element from the other element. For example, a first element may be named a second element without departing from the scope of the present invention. Likewise, a second element may be named a first element.

When it is said that one element is described as being "connected" or "coupled" to the other element, one element may be directly connected or coupled to the other element, but it should be understood that another element may be present between the two elements. In contrast, when it is said that one element is described as being "directly connected" or "directly coupled" to the other element, it should be understood that another element is not present between the two elements. In the same manner as above, when it is said that one element is described as being "between", "just between", "adjacent to" or "directly adjacent to", it should be understood that another element is present between the two element.

Terms used in this application are used to only describe specific exemplary embodiments and are not intended to restrict the present invention. An expression referencing a singular value additionally refers to a corresponding expression of the plural number, unless explicitly limited otherwise by the context. In this application, terms, such as "comprise", "include", or 'have", are intended to designate those characteristics, numbers, steps, operations, elements, or parts which are described in the specification, or any combination of them that exist, and it should be understood that they do not preclude the possibility of the existence or possible addition of one or more additional characteristics, numbers, steps, operations, elements, or parts, or combinations thereof.

All terms used herein, including technical or scientific terms, unless otherwise defined, have the same meanings which are typically understood by those having ordinary skill in the art. The terms, such as ones defined in common dictionaries, should be interpreted as having the same meanings as terms in the context of pertinent technology, and should not be interpreted as having ideal or excessively formal meanings unless clearly defined in the specification.

Hereinafter, the present invention is disclosed with reference to the attached drawings wherein the corresponding parts in the embodiments of the present invention are indicated by corresponding reference numerals and the repeated explanation on the corresponding parts will be avoided. If it is determined that the detailed explanation on the well known technology related to the present invention makes the scope of the present invention not clear, the explanation will be avoided for the brevity of the description.

FIG. 1 is a perspective view showing an endoscope.

As shown in FIG. 1, an endoscope 1 includes a grip part 2 held by a surgeon's hand, a control part 3 for controlling various parts, a control cable 4 for outputting images and for receiving control signals, an insertion part 5 inserted into a patient body, and a channel port 6 for supplying various fluids to the insertion part 5 or for inserting biopsy forceps 20 thereinto. In this case, the surgeon is a doctor who performs an endoscopic surgery, and the patient is a person who has the endoscopic surgery.

In a state where the grip part 2 is held by the surgeon, the insertion part 5 is inserted into the patient's body, and at this time, the control part 3 is controlled by the surgeon, while a monitor device (not shown) connected to the control cable 4 is being observed. Through the control of the control part 3 by the surgeon, for example, a light (not shown) is turned on, imaging is performed, or specific fluids are injected into the patient's body. The fluids include, for example, a cleaning liquid, a bubble remover, air, and so on. The fluids are selectively supplied to the insertion part 5 through the channel port 6, and if necessary, they are appropriately fed to the patient's body according to the selection of the surgeon. The present invention relates to the fluid supply device 10 coupled to the channel port 6 of the endoscope 1, and hereinafter, an explanation on the fluid supply device 10 for the endoscope according to the present invention will be in detail given with reference to FIGS. 2 to 9.

Figure 2:
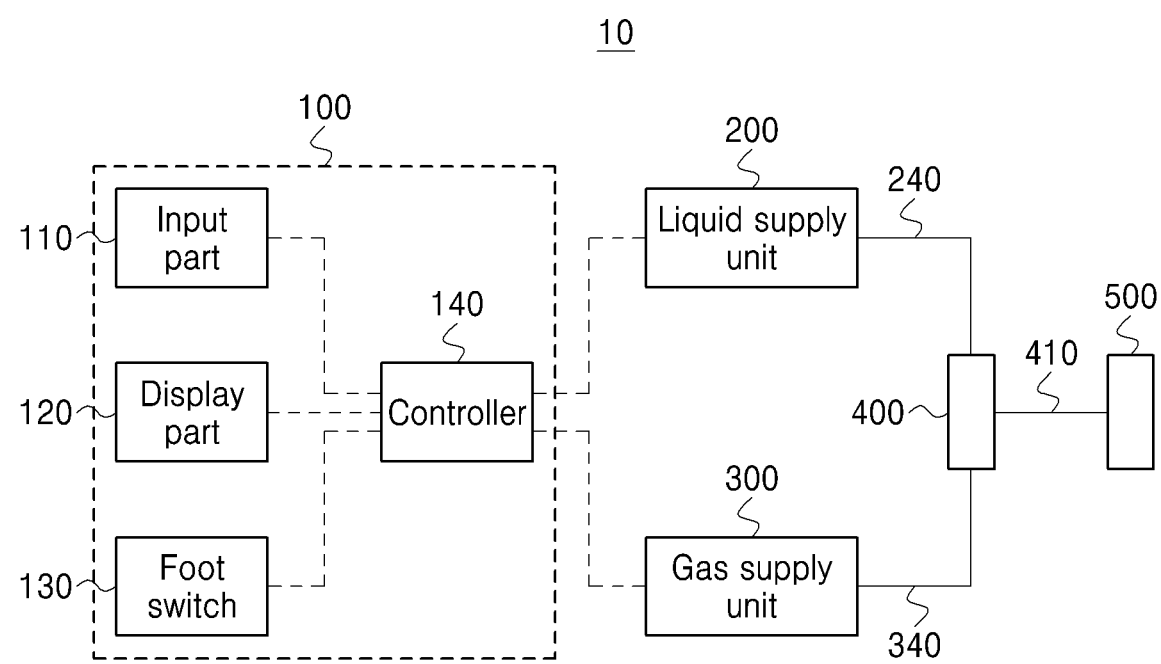
FIG. 2 is a block diagram showing a fluid supply device for an endoscope according to the present invention.
Figure 3:
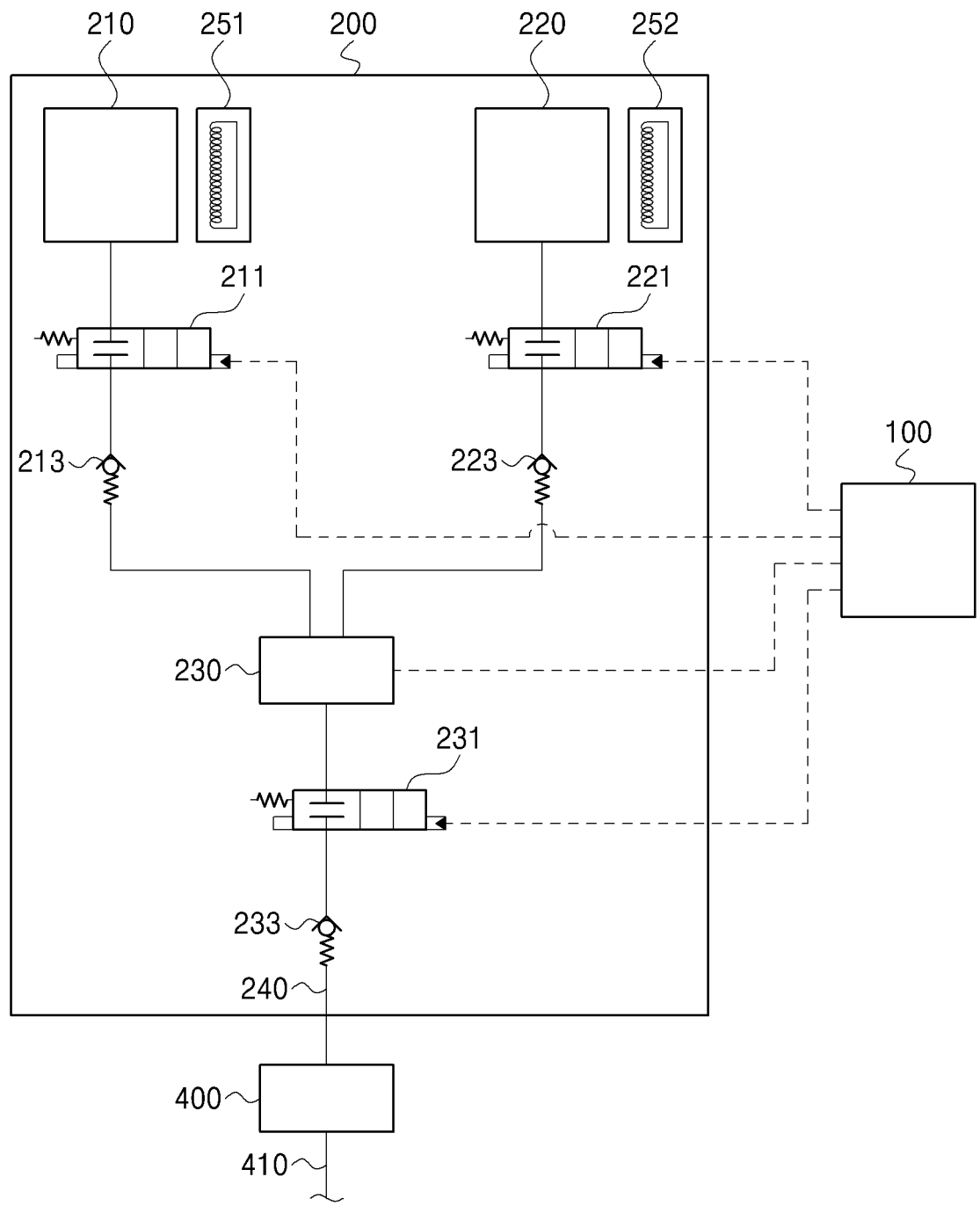
FIG. 3 is a circuit diagram showing a liquid supply unit of FIG. 2.
Figure 4:
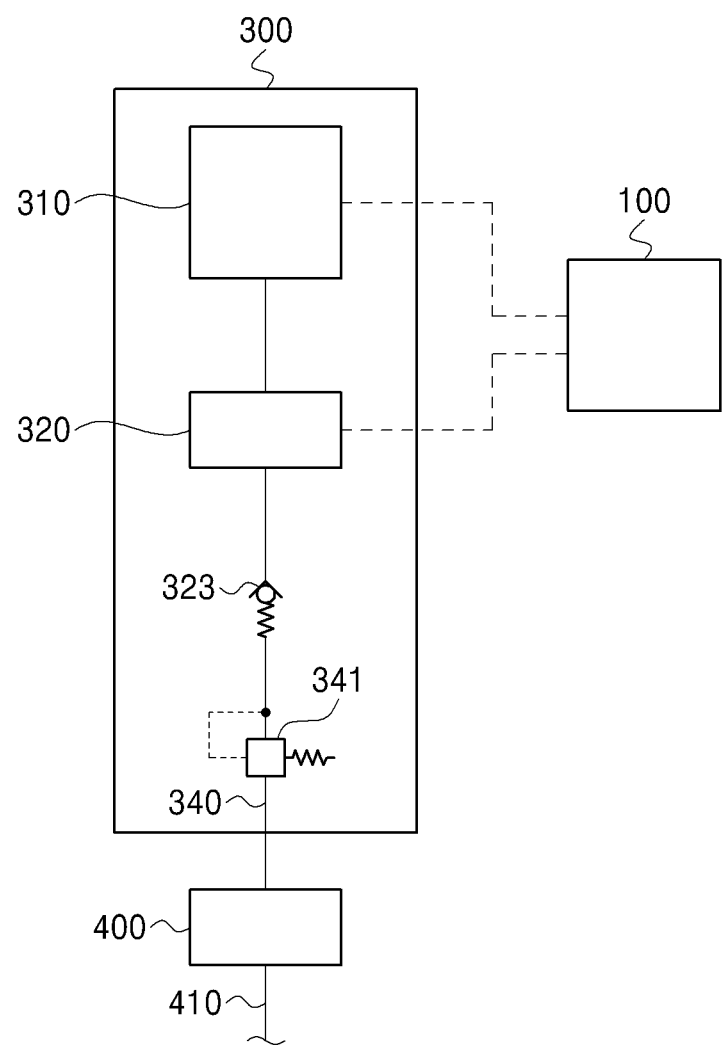
FIG. 4 and FIG. 5 are circuit diagrams showing a gas supply unit of FIG. 2.
Figure 5:
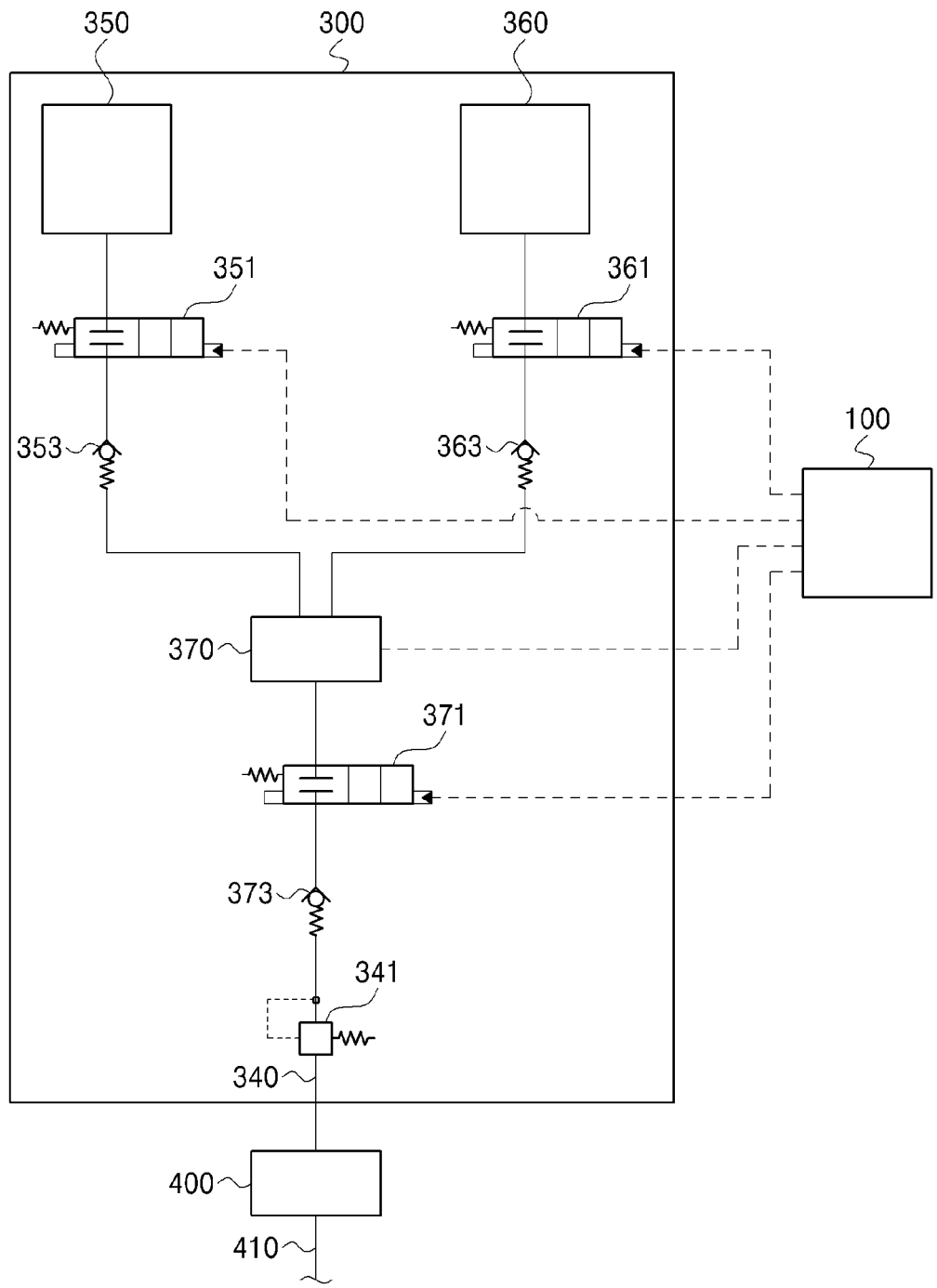
Figure 6:
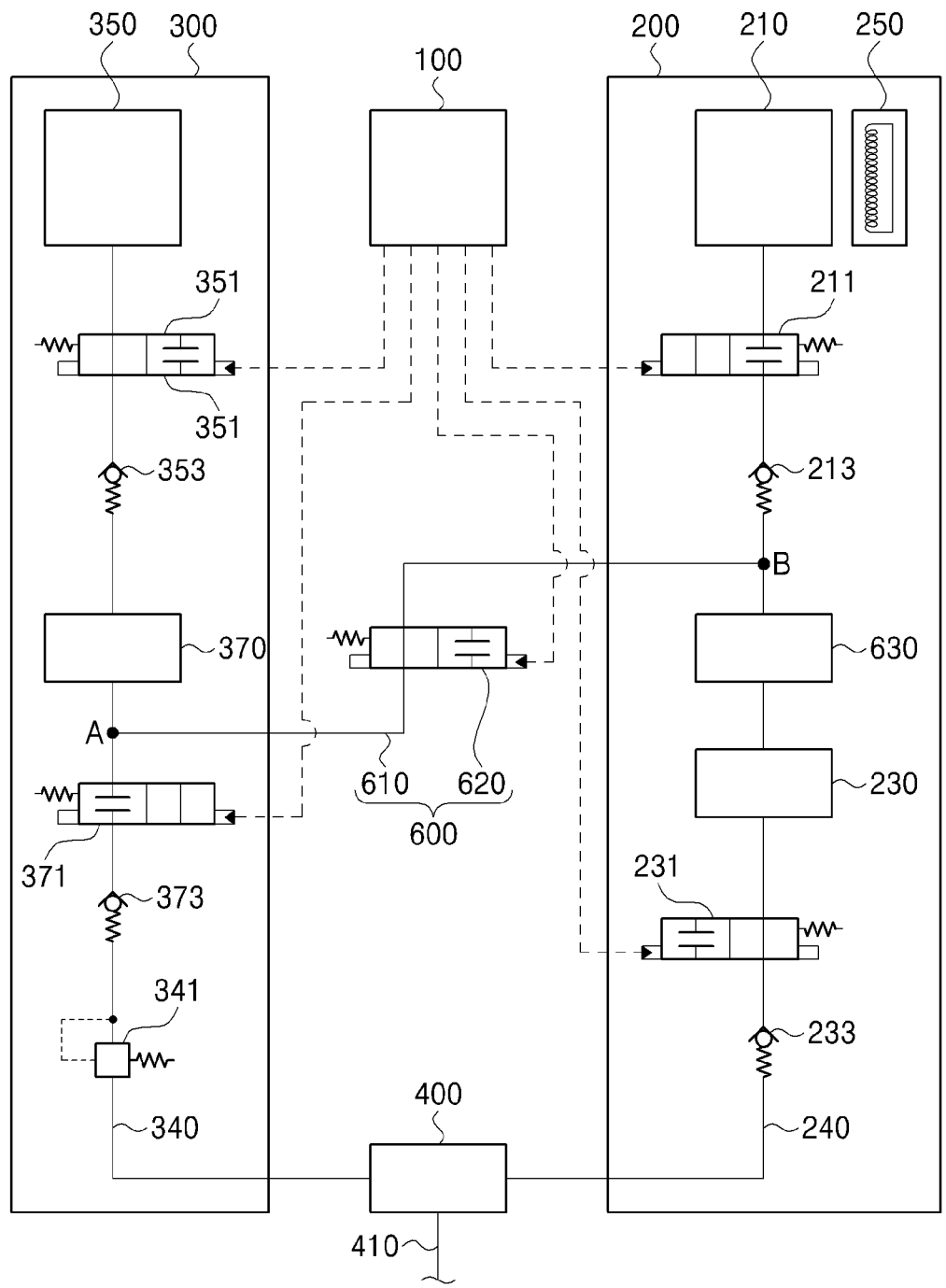
FIG. 6 is a circuit diagram showing a bypass unit for removing a residual liquid.
Figure 7:
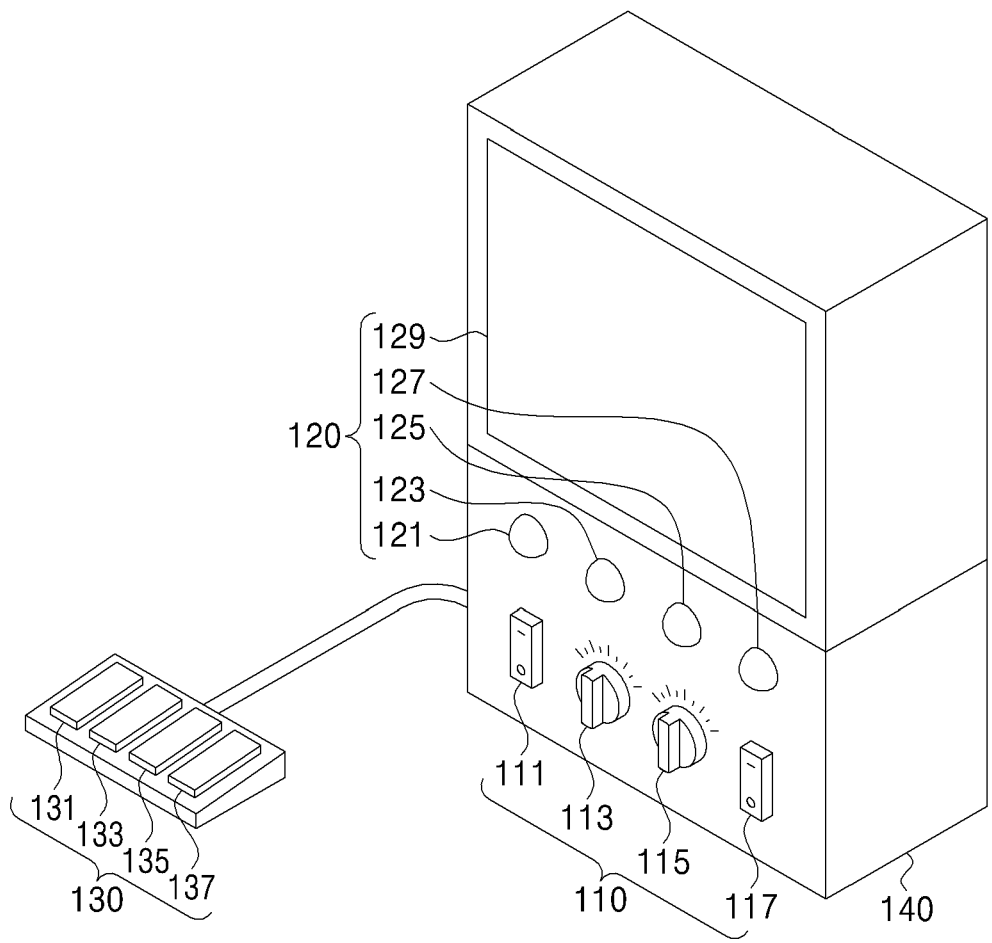
FIG. 7 is a perspective view showing a control unit of FIG. 2.
Figure 8:
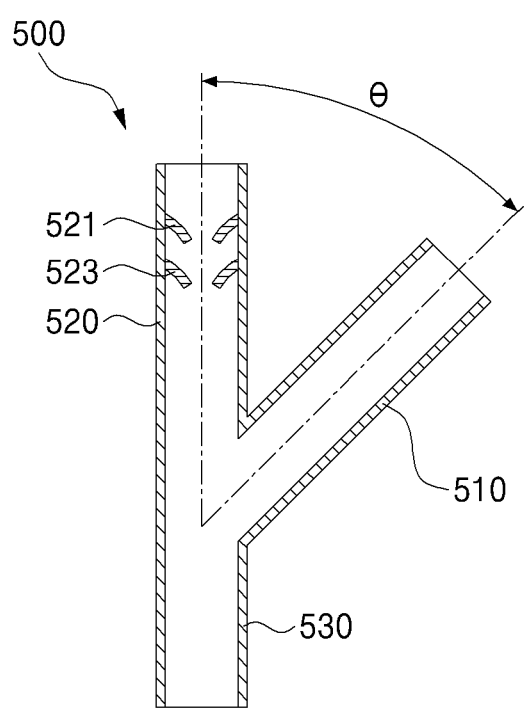
FIG. 8 is a sectional view showing a connecting unit of FIG. 1.
Figure 9:
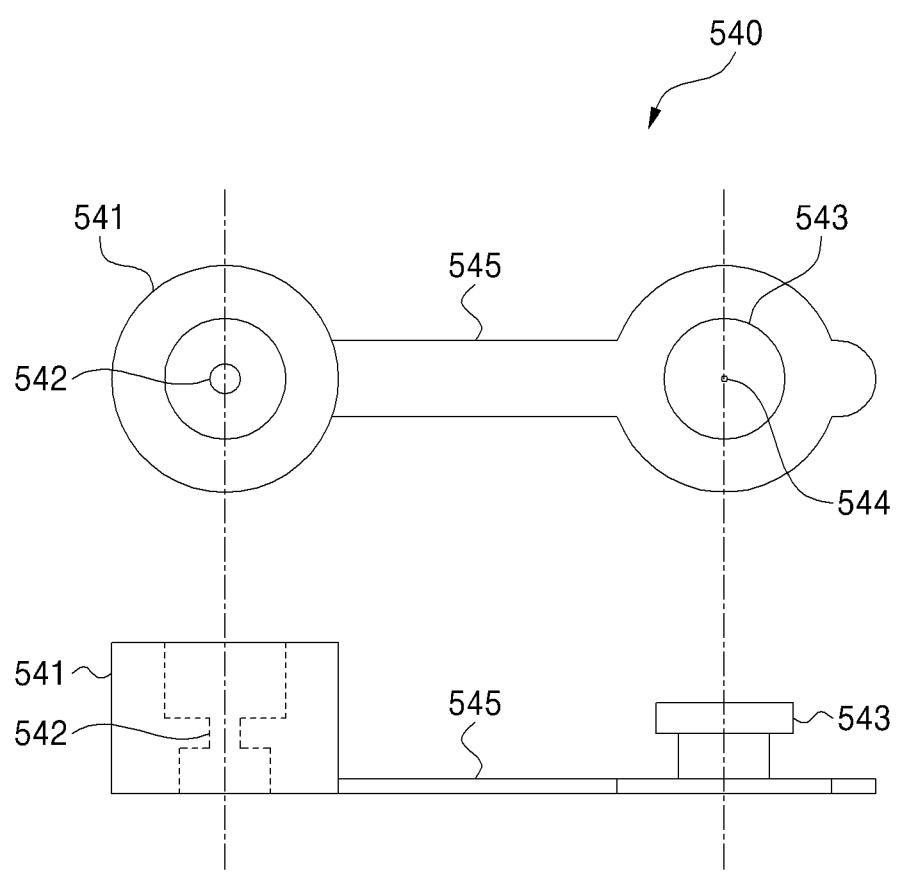
FIG. 9 is a view showing an input terminal stopper of the connecting unit.

FIG. 2 is a block diagram showing a fluid supply device for an endoscope according to the present invention, FIG. 3 is a circuit diagram showing a liquid supply unit of FIG. 2, FIGS. 4 and 5 are circuit diagrams showing a gas supply unit of FIG. 2, FIG. 6 is a circuit diagram showing a bypass unit for removing a residual liquid, FIG. 7 is a perspective view showing a control unit of FIG. 2, FIG. 8 is a sectional view showing a connecting unit of FIG. 1, and FIG. 9 is a view showing an input terminal stopper of the connecting unit.

Referring first to FIGS. 2 to 7, the fluid supply device 10 for the endoscope according to the present invention includes a liquid supply unit 200 for supplying liquids, a gas supply unit 300 for supplying gases, and a control unit 100 for controlling operations of the liquid supply unit 200 and the gas supply unit 300.

The liquid supply unit 200 is adapted to selectively supply the liquids to the endoscope 1. For example, the liquids include a cleaning liquid like a saline solution, a bubble remover for removing gas in the intestines like Gasocol Suspension, and a dye for dyeing a diseased area. The liquid supply unit 200 supplies an amount of liquid needed to the endoscope 1 according to the control of the control unit 100 by the surgeon.

As shown in FIG. 3, the liquid supply unit 200 includes first and second liquid tanks 210 and 220 for storing the liquids, a liquid pump 230 for supplying the liquids stored in the first and second liquid tanks 210 and 220 to the endoscope 1, first to third opening and closing valves 211, 221, and 231 for opening and closing flow paths, and first to third backflow prevention valves 213, 223, and 233 for preventing the liquids from flowing back.

The first liquid tank 210 and the second liquid tank 220 store the first liquid and the second liquid. At this time, the first liquid and the second liquid can be different from each other. For example, the first liquid is a saline solution, and the second liquid is a bubble remover or a saline solution containing a bubble remover. If cleaning is needed, the liquid supply unit 200 supplies the first liquid to the endoscope 1, and if it is necessary to get out of gas in the intestines, the liquid supply unit 200 supplies the second liquid to the endoscope 1. Otherwise, of course, the first liquid and the second liquid may be the same as each other.

On a flow path connecting the first liquid tank 210 and the liquid pump 230, the first opening and closing valve 211 and the first backflow prevention valve 213 are located, and on a flow path connecting the second liquid tank 220 and the liquid pump 230, the second opening and closing valve 221 and the second backflow prevention valve 223 are located. The first and second opening and closing valves 211 and 221 serve to open or close the corresponding flow paths, and the first and second backflow prevention valves 213 and 223 serve to prevent the liquids from flowing back to the first and second liquid tanks 210 and 220.

In this case, the first and second opening and closing valves 211 and 221 can be controlled by means of the control unit 100. If a foot switch 130 of the control unit 100 is operated by the surgeon, in more detail, a controller 140 of the control unit 100 transmits a flow path opening signal to the first opening and closing valve 211 or the second opening and closing valve 221. Even if the control part 3 of the endoscope 1 is not operated by the surgeon, accordingly, the kind of liquid needed for the endoscopic surgery can be easily selected by means of the foot of the surgeon.

The liquid pump 230 serves to supply the liquid stored in the first liquid tank 210 or the second liquid tank 220 to the endoscope 1 through the channel port 6. The liquid pump 230 can be operated by means of the control unit 100. In detail, if the foot switch 130 is operated by the surgeon, the controller 140 transmits an operating signal to the liquid pump 230. Accordingly, the operation of the liquid pump 230 is controlled by the operation of the foot switch 130, thereby controlling whether the liquid is supplied.

Further, an amount of liquid discharged through the liquid pump 230 can be controlled by means of the control unit 100. If a desired amount of liquid discharged is set through a first input dial 113 of an input part 110 of the control unit 100, in detail, an intensity of current applied to the liquid pump 230 is controlled by means of the controller 140, thereby controlling the amount of liquid discharged through the liquid pump 230.

The liquid discharged through the liquid pump 230 is supplied to the channel port 6 through a liquid supply flow path 240. On the liquid supply flow path 240, the third opening and closing valve 231 and the third backflow prevention valve 233 are located. The third opening and closing valve 231 serves to open or close the liquid supply flow path 240 according to the control signal of the control unit 100, and the third backflow prevention valve 233 serves to prevent the liquid discharged from the liquid pump 230 from flowing back to the liquid pump 230.

In this case, the third opening and closing valve 231 can be controlled by means of the control unit 100. If the foot switch 130 is operated by the surgeon, in more detail, the controller 140 transmits a flow path opening signal to the third opening and closing valve 231. Even if the control part 3 of the endoscope 1 is not operated by the surgeon, accordingly, whether the liquid needed for the endoscopic surgery is supplied can be easily controlled by means of the foot of the surgeon.

According to the present invention, the first to third opening and closing valves 211, 221, and 231 are solenoid valves that are controlled by current signals.

According to the present invention, the liquid supply unit 200 further includes a temperature adjustment part 250 for adjusting temperatures of the liquids supplied to the endoscope 1.

For example, the temperature adjustment part 250 includes a first temperature adjuster 251 for constantly maintaining a given temperature of the liquid stored in the first liquid tank 210 and a second temperature adjuster 252 for constantly maintaining a given temperature of the liquid stored in the second liquid tank 220.

In this case, the first temperature adjuster 251 and the second temperature adjuster 252 come into contact with the first liquid tank 210 and the second liquid tank 220 or are adjacent thereto. Otherwise, they can be adjacent to the liquid supply flow path 240 from which the liquid is supplied. Further, the first temperature adjuster 251 and the second temperature adjuster 252 may become heaters for heating the stored liquids or coolers for cooling them.

The temperature adjustment part 250 serves to control the stored liquids in the first and second liquid tanks 210 and 220 or the liquids flowing along the liquid supply flow path 240 so that the liquids can be kept at the given temperatures, and after adjusted to optimal temperatures, they are supplied to the patient through the endoscope 1.

Even though the surgeon's hand is not used, as mentioned above, the liquid supply can be controlled by the use of the surgeon's foot. In detail, the first opening and closing valve 211 and the second opening and closing valve 221 are selectively open and closed, thereby selecting the kind of liquid supplied, and the third opening and closing valve 231 is selectively open and closed, thereby controlling whether the liquid is supplied. Further, an amount of liquid discharged can be adjusted by means of the control of the liquid pump 230. Such control can be performed by the control of the foot switch 130 and the input part 110. Accordingly, there is no need to provide an additional surgical assistant for supplying liquids, and the number of parts operated by the surgeon's hand can be reduced, thereby performing the endoscopic surgery in more stable and rapid manners.

On the other hand, as shown in FIG. 3, the liquid supply unit 200 has the two liquid tanks 210 and 220, and that is, it selectively supplies only two kinds of liquids. According to the present invention, however, the liquid supply unit 200 is not limited particularly thereto. The liquid supply unit 200 supplies only one kind of liquid or selectively supplies three or more kinds of liquids. For example, the liquid supply unit 200 further includes a dye tank (not shown), and in this case, the liquid supply unit 200 selectively supplies the cleaning liquid, the bubble remover, the dye, and other liquids used for the endoscopic surgery.

Further, as shown in FIG. 3, one liquid pump 230 selectively supplies the two kinds of liquids, but according to the present invention, however, the liquid pump 230 is not limited particularly thereto. For example, the liquid supply unit 200 includes a plurality of liquid tanks in which different kinds of liquids are stored and a plurality of liquid pumps, and each liquid pump can discharge only one kind of liquid.

The gas supply unit 300 selectively supplies various gases to the endoscope 1. For example, the gases include air, oxygen, carbon dioxide, and so on. The air is used for the endoscopic surgery of the stomach, the concentrated oxygen for the endoscopic surgery of the bronchi, and the carbon dioxide for the endoscopic surgery of the large intestine. However, different kinds of gases may be used for the respective endoscopic surgeries, and otherwise, various kinds of gases may be used together.

The gas supply unit 300 selectively supplies an amount of gas needed to the endoscope 1. Now, an explanation on examples of the gas supply unit 300 according to the present invention will be in more detail given with reference to FIGS. 4 and 5.

As shown in FIG. 4, first, the gas supply unit 300 includes a bubble generator 310 for producing bubbles, a blower 320 for supplying the produced bubbles to the endoscope 1, and a fourth backflow prevention valve 323 for limiting the flow of bubbles through a flow path in one direction.

Instead of the 'flow path', by the way, a tube, a duct, and so on can be used as a path along which the gas of the gas supply unit 300 is moved, but for the brevity of the description, the path along which the gas is moved is also called 'flow path'.

The bubble generator 310 serves to produce bubbles of air or oxygen from air in the atmosphere. The bubble generator 310 is operated by means of the control of the control unit 100. Further, the sizes or shapes of the bubbles can be controlled by means of the control unit 100 according to the control of the surgeon.

The blower 320 serves to supply the bubbles produced from the bubble generator 310 to the endoscope 1 through the channel port 6. The blower 320 is operated by means of the control of the control unit 100. If the foot switch 130 is operated by the surgeon, in detail, the controller 140 transmits an operating signal to the blower 320. Accordingly, the blower 320 is operated or the operation of the blower 320 is stopped.

Further, an amount of gas discharged through the blower 320 can be controlled by means of the control unit 100. If a desired amount of gas discharged is set through a second input dial 115 of the input part 110 of the control unit 100, in detail, an intensity of current applied to the blower 320 is controlled by means of the controller 140, thereby controlling the amount of gas discharged through the blower 320.

The gas discharged through the blower 320 is supplied to the channel port 6 through a gas supply flow path 340. On the gas supply flow path 340, the fourth backflow prevention valve 323 and a pressure adjustment valve 341 are located. The fourth backflow prevention valve 323 serves to prevent the gas discharged from the blower 320 from flowing back to the blower 320. In this case, a safety pressure is a value set by a manufacturer in a step of making the fluid supply device 10 for the endoscope or set by a surgeon in a step of performing endoscopic surgery, which is an upper pressure limit value of the gas supply flow path 340 for preventing safety accidents from occurring. If a pressure of the gas supply flow path 340 reaches a predetermined safety pressure, the pressure adjustment valve 341 allows the gas supply flow path 340 to communicate with the outside (the atmosphere), thereby preventing the internal pressure of the gas supply flow path 340 from being excessively raised.

As mentioned above, even though the surgeon's hand is not used, the gas supply can be controlled by the use of the surgeon's foot. In detail, the operations of the bubble generator 310 and the blower 320 are controlled, thereby controlling the supply of gas and the supply speed of gas. Such control can be performed by the control of the foot switch 130 and the input part 110. Accordingly, there is no need to provide an additional surgical assistant for supplying liquids, and the number of parts operated by the surgeon's hand can be reduced, thereby performing the endoscopic surgery in more stable and rapid manners.

By the way, the gas supply unit 300 as shown in FIG. 4 can be adopted in case of using air or oxygen contained in large quantities in air. However, in case of using gases not contained in air or whose density is low, separate storage tanks may be provided. An example in which the storage tanks are adopted is shown in FIG. 5.

As shown in FIG. 5, the gas supply unit 300 includes first and second gas tanks 350 and 360 for storing gases, a gas pump 370 for supplying the gases stored in the first and second gas tanks 350 and 360 to the endoscope 1, fourth to sixth opening and closing valves 351, 361, and 371 for opening and closing flow paths, and fifth to seventh backflow prevention valves 353, 363, and 373 for preventing the gases from flowing back.

The first gas tank 350 and the second gas tank 360 store a first gas and a second gas. At this time, the first gas and the second gas can be different from each other. For example, the first gas is air, and the second gas is carbon dioxide.

On a flow path connecting the first gas tank 350 and the gas pump 370, the fourth opening and closing valve 351 and the fifth backflow prevention valve 353 are located, and on a flow path connecting the second gas tank 360 and the gas pump 370, the fifth opening and closing valve 361 and the sixth backflow prevention valve 363 are located. The fourth and fifth opening and closing valves 351 and 361 serve to open or close the corresponding flow paths, and the fifth and seventh backflow prevention valves 353 and 363 serve to prevent the gases from flowing back to the first and second gas tanks 350 and 360.

In this case, the fourth and fifth opening and closing valves 351 and 361 can be controlled by means of the control unit 100. If the foot switch 130 of the control unit 100 is operated by the surgeon, in more detail, the controller 140 of the control unit 100 transmits a flow path opening signal to the fourth opening and closing valve 351 or the fifth opening and closing valve 361. Even if the control part 3 of the endoscope 1 is not operated by the surgeon's hand, accordingly, the kind of gas needed for the endoscopic surgery can be easily selected by means of the foot of the surgeon.

The gas pump 370 serves to supply the gas stored in the first gas tank 350 or the second gas tank 360 to the endoscope 1 through the channel port 6. The gas pump 370 can be operated by means of the control unit 100. In detail, if the foot switch 130 is operated by the surgeon, the controller 140 transmits an operating signal to the gas pump 370. Accordingly, the operation of the gas pump 370 is controlled by the operation of the foot switch 130, thereby controlling whether the gas is supplied.

Further, an amount of gas discharged through the gas pump 370 can be controlled by means of the control unit 100. If a desired amount of gas discharged is set through the second input dial 115 of the input part 110 of the control unit 100, in detail, an intensity of current applied to the gas pump 370 is controlled by means of the controller 140, thereby controlling the amount of gas discharged through the gas pump 370.

The gas discharged through the gas pump 370 is supplied to the channel port 6 through a gas supply flow path 340. On the gas supply flow path 340, the sixth opening and closing valve 371, the seventh backflow prevention valve 373, and a pressure adjustment valve 341 are located. The sixth opening and closing valve 371 serves to open or close the gas supply flow path 340 according to the control signal of the control unit 100. The seventh backflow prevention valve 373 serves to prevent the gas discharged from the gas pump 370 from flowing back to the gas pump 370. The pressure adjustment valve 341 allows the gas supply flow path 340 to communicate with the outside (the atmosphere) if a pressure of the gas supply flow path 340 reaches a predetermined safety pressure, thereby preventing the internal pressure of the gas supply flow path 340 from being excessively raised.

In this case, the sixth opening and closing valve 371 can be controlled by means of the control unit 100. If the foot switch 130 is operated by the surgeon, in more detail, the controller 140 transmits a flow path opening signal to the sixth opening and closing valve 371. Even if the control part 3 of the endoscope 1 is not operated by the surgeon's hand, accordingly, whether the gas needed for the endoscopic surgery is supplied can be easily controlled by means of the foot of the surgeon.

According to the present invention, the fourth to sixth opening and closing valves 351, 361, and 371 are solenoid valves that are controlled by current signals.

Even though the surgeon's hand is not used, as mentioned above, the gas supply can be controlled by the use of the surgeon's foot. In detail, the fourth opening and closing valve 351 and the fifth opening and closing valve 361 are selectively open and closed, thereby selecting the kind of gas supplied, and the sixth opening and closing valve 371 is selectively open and closed, thereby controlling whether the gas is supplied. Further, an amount of gas discharged can be adjusted by means of the control of the gas pump 370. Such control can be performed by the control of the foot switch 130 and the input part 110. Accordingly, there is no need to provide an additional surgical assistant for supplying gases, and the number of parts operated by the surgeon's hand can be reduced, thereby performing the endoscopic surgery in more stable and rapid manners.

On the other hand, as shown in FIG. 5, the gas supply unit 300 has the two gas tanks 350 and 360, and that is, it selectively supplies only two kinds of gases. According to the present invention, however, the gas supply unit 300 is not limited particularly thereto. The gas supply unit 300 supplies only one kind of gas or selectively supplies three or more kinds of gases. For example, the gas supply unit 300 further includes an oxygen tank (not shown), and in this case, the gas supply unit 300 selectively supplies air, carbon dioxide, and oxygen.

Further, as shown in FIG. 5, one gas pump 370 selectively supplies the two kinds of gases, but according to the present invention, however, the gas pump 370 is not limited particularly thereto. For example, the gas supply unit 300 includes a plurality of gas tanks in which different kinds of gases are stored and a plurality of gas pumps, and each gas pump can discharge only one kind of gas.

Further, the fluid supply device 10 for the endoscope according to the present invention can selectively supply the liquid and the gas to the endoscope 1. If the liquid is supplied at the last procedure of the endoscopic surgery, it is in a state of being filled into the liquid supply flow path 240 and an output flow path 410 as will be discussed later.

By the way, the state where the liquid is filled into the liquid supply flow path 240 and the output flow path 410 does not matter if the endoscopic surgery is continuously carried out, but it matters if there is a time interval between present and next endoscopic surgeries. This is because the liquid filled in the flow paths may be contaminated or degenerated. To prevent such state, all flow paths used are thrown away after the endoscopic surgery has been finished, but in this case, undesirably, resources waste is caused, thereby raising a cost of the endoscopic surgery. So as to solve the above-mentioned problems, according to the present invention, the gas supply flow path 340 and the liquid supply flow path 240 are connected to each other to allow the liquid in the liquid supply flow path 240 to be clearly removed by means of the gas, so that an interior of the liquid supply flow path 240 is completely dried. The example is shown in FIG. 6.

As shown in FIG. 6, a fluid supply device 10 for an endoscope according to another embodiment of the present invention includes a liquid supply unit 200 for supplying liquids, a gas supply unit 300 for supplying gases, a bypass unit 600 for selectively connecting the gas supply unit 200 and the liquid supply unit 200 to each other, and a control unit 100 for controlling operations of the liquid supply unit 200, the gas supply unit 300, and the bypass unit 600.

On the other hand, the liquid supply unit 200 and the gas supply unit 300 are substantially the same as or similar to those as shown in FIGS. 2 to 5. Accordingly, parts of the liquid supply unit 200 and the gas supply unit 300 have the same reference numerals as used in FIGS. 3 and 5, and the repeated explanations on them will be avoided. Further, the control unit 100 will be discussed later, and first, the bypass unit 600 will be explained below.

The bypass unit 600 includes a bypass flow path 610 for connecting a liquid supply flow path 240 and a gas supply flow path 340 to each other, a bypass flow pass opening and closing valve 620 for selectively opening and closing the bypass flow path 610, and a suction pump 630 for moving the gas in the gas supply flow path 340 to the liquid supply flow path 240.

According to the present invention, one end A of the bypass flow path 610 is connected to the downstream flow under the gas pump 370, and the other end B of the bypass flow path 610 is connected to the upstream flow above the liquid pump 230. At this time, the 'upstream' and 'downstream' flows are defined with respect to the flows of the fluids moving from a gas tank 350 and a liquid tank 210. That is, places relatively close to the gas tank 350 and the liquid tank 210 are called the 'upstream flow', and places relatively distant therefrom the 'downstream flow'.

One end A of the bypass flow path 610 is connected to the downstream flow under the gas pump 370, which means that one end A of the bypass flow path 610 is connected between the gas pump 370 and a connector 400 as will be discussed later. If one end A of the bypass flow path 610 is connected to the upstream flow above the gas pump 370, the gas is not supplied gently from the bypass flow path 610, so that the suction pump 630 as will be discussed later cannot move the gas stored in the first gas tank 350 to the liquid supply flow path 240. Accordingly, one end A of the bypass flow path 610 is desirably connected to the downstream flow under the gas pump 370.

The other end B of the bypass flow path 610 is connected to the upstream flow above the liquid pump 230, which means that the other end B of the bypass flow path 610 is connected between the first liquid tank 210 and the liquid pump 230. If the other end B of the bypass flow path 610 is connected to the downstream flow under the liquid pump 230, the liquid filled into the liquid pump 230 is not discharged to the outside. Accordingly, the other end B of the bypass flow path 610 is desirably connected to the upstream flow above the liquid pump 230.

The bypass flow pass opening and closing valve 620 is located on the bypass flow path 610 and is a solenoid valve that is controlled by the current signal transmitted from the control unit 100. If a liquid removal function is selected by the control of the control unit 100 of the surgeon, the gas is supplied through the bypass unit 600 to allow the liquid in the liquid supply flow path 240 to be removed and further to allow the interior of the liquid supply flow path 240 to be completely dried.

In detail, the first opening and closing valve 211 on the liquid supply flow path 240 is closed, and the third opening and closing valve 231 thereon is open. Further, the fourth opening and closing valve 351 on the gas supply flow path 340 is open, and the sixth opening and closing valve 371 thereon is closed. Furthermore, the bypass flow pass opening and closing valve 620 on the bypass flow path 610 is open, and the suction pump 630 is operated. Accordingly, the gas stored in the first gas tank 350 is supplied to the liquid supply flow path 240 through the bypass flow path 610. The gas supplied to the liquid supply flow path 240 pushes the liquid filled in the liquid supply flow path 240. As a result, the liquid in the liquid supply flow path 240 is all removed, and the interior of the liquid supply flow path 240 is completely dried.

On the other hand, the liquid pump 230 is a pump for discharging the liquid, and in a state where the liquid is not filled in the liquid pump 230, by the way, the liquid pump 230 cannot discharge the liquid normally. According to the present invention, the suction pump 630 as a gas pump is additionally provided to control the gas supply through the bypass flow path 610. The suction pump 630 may be located on the bypass flow path 610 or on the liquid supply flow path 240. The suction pump 630 provides a suction force with which the gas stored in the first gas tank 350 is moved to the liquid supply flow path 240 through the bypass flow path 610. If a pump capable of gently supplying both of liquid and gas is used, on the other hand, the suction pump 630 is not needed additionally. In this case, the liquid and the gas can be selectively discharged by means of one pump located on the liquid supply flow path 240.

According to an alternative embodiment of the present invention, the fluid supply device 10 for the endoscope according to the present invention includes a bubble generator (not shown) located on the liquid supply flow path 240, instead of the bypass unit 600 for selectively connecting the liquid supply flow path 240 and the gas supply flow path 340 to each other. In detail, the liquid supply flow path 240 is not dried by means of the gas stored in the first gas tank 350 but dried by means of the bubble generator located on the liquid supply flow path 240. In this case, the bubble generator can be located at the same position as the suction pump 630 as shown in FIG. 6.

As shown in FIGS. 2 and 7, the control unit 100 includes the input part 110 and the foot switch 130 for receiving control commands from the surgeon, the controller 140 for controlling the operations of the liquid supply unit 200, the gas supply unit 300, and the bypass unit 600 according to the control commands, and a display part 120 for transmitting information on the operations of the liquid supply unit 200, the gas supply unit 300, and the bypass unit 600 to the surgeon.

The input part 110 serves to control the whole operations of the fluid supply device 10. For example, the input part 110 includes a power switch 111 for turning on/off the fluid supply device 10, the first input dial 113 for adjusting an amount of liquid discharged from the liquid supply unit 200, the second input dial 115 for adjusting an amount of gas discharged from the gas supply unit 300, and a temperature adjustment switch 117 for turning on/off the temperature adjustment part 250. The amount of liquid or gas discharged can be adjusted by means of the control of the first input dial 113 or the second input dial 115 of the surgeon. Accordingly, the amount of liquid or gas discharged can be adjusted according to a skill level of the surgeon. Further, a given temperature of the liquid supplied can be constantly maintained by means of the temperature adjustment switch 117.

The display part 120 serves to transmit the information on the current operation of the fluid supply device 10 to the surgeon. For example, the display part 120 includes a power lamp 121 for indicating information on whether the fluid supply device 10 is turned on/off, a liquid supply lamp 123 for indicating liquid supply, a gas supply lamp 125 for indicating gas supply, and a temperature adjustment lamp 127 for indicating information on an operation of the temperature adjustment part 250.

Further, the display part 120 can audibly transmit information on the fluid currently supplied to the surgeon. For example, the display part 120 includes a speaker that provides sound information on the kind of fluid currently supplied, the supply speed, the total amount of fluid supplied, the temperature of fluid, and start and stop of fluid supply for the surgeon.

According to the present invention, the display part 120 further includes a display member 129 for visibly displaying information. The display member 129 can provide information on the kind of fluid currently supplied, the supply speed, and the temperature of fluid for the surgeon.

According to the present invention, the display part 120 can display state information like vital sign of the patient. For example, the controller 140 receives the patient's health state information from the endoscope 1 or other medical devices through radio communication, and the received information is displayed on the display member 129. For example, the health state information includes the patient's oxygen saturation, pulse rate, body temperature, blood pressure, and so on.

While the endoscopic surgery is being carried out, various medical equipment may be simultaneously used, and in this case, the surgeon checks the various medical equipment at a time to recognize the state of the patient. According to the present invention, however, the information on the various medical equipment can be displayed at a time on the display member 129, thereby providing many conveniences for the surgeon and rapidly treating unexpected changes in the patient's state.

On the other hand, as shown in FIG. 7, the input part 110 and the display part 120 have the four input members 111, 113, 115, and 117 and the four display members 121, 123, 125, and 127. According to the present invention, however, they are not limited particularly thereto, and they may be appropriately changed according to the kind of information inputted, the input type, the kind of display information, and the display type.

The foot switch 130 is located on the floor of an operating room where the endoscopic surgery is carried out and has a plurality of selection switches. If the selection switches are pressed by the surgeon's foot, the functions connected to the corresponding switches can be selected. For example, the foot switch 130 includes a liquid supply switch 131 for supplying the liquid to the endoscope 1, a gas supply switch 133 for supplying the gas to the endoscope 1, a clean switch 135 for removing the liquid in the liquid supply flow path 240 through the bypass unit 600 to thus dry the interior of the liquid supply flow path 240, a constant temperature switch 137 for operating the temperature adjustment part 250, a liquid selection switch (not shown) for selecting the kind of liquid supplied, and a gas selection switch (not shown) for selecting the kind of gas supplied. If one of the selection switches is pressed by the surgeon's foot, a control signal corresponding to the pressed selection switch is generated and transmitted to the controller 140. Further, the number of selection switches and the shapes of the selection switches of the foot switch 130 may be appropriately changed if necessary.

The kind of fluid supplied and the supply timing of the fluid can be easily selected by means of the control of the foot switch 130 during the endoscopic surgery. Accordingly, the fluids needed for the endoscopic surgery can be easily and rapidly supplied, without any separate surgical assistant.

According to the present invention, the fluid supply device 10 for the endoscope according to the present invention further includes the connector 400 for connecting the liquid supply unit 200 and the gas supply unit 300 to the channel port 6.

For example, the connector 400 is a Y-shaped connector having two input terminals and one output terminal. The two input terminals are connected to the liquid supply flow path 240 of the liquid supply unit 200 and to the gas supply flow path 340 of the gas supply unit 300. The output terminal has the output flow path 410, and the output flow path 410 is connected to the channel port 6 of the endoscope 1. The fluid supplied to the liquid supply flow path 240 or the gas supply flow path 340 is supplied to the endoscope 1 through the output flow path 410 of the connector 400. In this case, the output flow path 410 is formed of a single channel or a plurality of channels according to the kinds of fluids used.

In a process where the liquid is removed from the interior of the liquid supply flow path 240 by means of the bypass unit 600, however, the output terminal of the connector 400 has to be not connected to the endoscope 1.

During the endoscopic surgery, on the other hand, a biopsy in which a piece of tissue is removed may be carried out so that it is examined or a simple surgery is performed. In this case, biopsy forceps 20 or surgical instruments are inserted into the endoscope 1 through the channel port 6.

However, the fluid supply device 10 is coupled to the channel port 6, and so as to perform the biopsy, accordingly, it has to be separated from the channel port 6. After the output flow path 410 of the fluid supply device 10 is separated from the channel port 6, in detail, the biopsy forceps 20 are inserted into the endoscope 1 through the channel port 6, and after the biopsy has been finished, the output flow path 410 has to be coupled to the channel port 6. So as to remove such inconveniences, the fluid supply device 10 according to the present invention further includes a connecting unit 500 through which the fluid supply and the insertion of the biopsy forceps 20 can be simultaneously carried out.

As shown in FIGS. 1, 8 and 9, the connecting unit 500 includes two input terminals 510 and 520, one output terminal 530, and an input terminal stopper 540.

The first input terminal 510 is coupled to the output flow path 410, and the output terminal 530 to the channel port 6 of the endoscope 1. Further, the second input terminal 520 is used as a path into which surgical instruments like the biopsy forceps 20 are inserted. If the biopsy is needed during the endoscopic surgery, accordingly, the surgical instruments like the biopsy forceps 20 are easily inserted into the endoscope 1, without any separation of the fluid supply device 10 from the endoscope 1. Only when it is necessary to open the second input terminal 520, the input terminal stopper 540 is removed from the second input terminal 520, thereby allowing the second input terminal 520 to be open.

According to the present invention, the second input terminal 520 has backflow prevention members 521 and 523 protruding from the inner peripheral surface thereof to prevent the fluid from flowing back.

If the biopsy forceps 20 are not used, the input terminal stopper 540 closes open one end of the second input terminal 520, and even though the fluid supplied to the first input terminal 510 flows back, accordingly, it does not matter. If the biopsy forceps 20 are used, however, the fluid supplied to the first input terminal 510 flows back to the second input terminal 520, so that it may leak to the outside. To prevent such backflow, the backflow prevention members 521 and 523 are provided to block a space between the biopsy forceps 20 and the inner peripheral surface of the second input terminal 520.

As shown in FIG. 8, the backflow prevention members 521 and 523 are circular members protruding inward from the inner peripheral surface of the second input terminal 520 in such a manner as to come into close contact with the biopsy forceps 20 inserted into the second input terminal 520 to prevent the fluid supplied to the first input terminal 510 from blowing back to the second input terminal 520. The backflow prevention members 521 and 523 are made of an elastic material like rubber, silicone, and so on, and further, two or more backflow prevention members may be provided to more reliably prevent the backflow of the fluid.

According to the present invention, an angle θ between the first input terminal 510 and the second input terminal 520 ranges from 30 to 45°.

If the angle between the two input terminals 510 and 520 is too big, the fluid may not flow gently. Contrarily, if it is too small, the first input terminal 510 may cause an interruption when the biopsy forceps 20 are inserted into the second input terminal 520. Accordingly, the angle between the two input terminals 510 and 520, which causes no interruption in the insertion of the biopsy forceps 20 and allows the gentle flow of the fluid to be kept, desirably ranges from 30 to 45°.

As shown in FIG. 9, the input terminal stopper 540 includes a body 541 detachably coupled to the second input terminal 520, a cap 543 detachably coupled to the body 541, and a connector 545 for connecting the body 541 and the cap 543.

A first opening 542 is formed on a center of the body 541, and a second opening 544 on a center of the cap 543. At this time, the first opening 542 is larger than the second opening 544. In detail, the first opening 542 and the second opening 544 can be selectively used according to the sizes of the surgical instruments inserted into the second input terminal 520.

Further, the input terminal stopper 540 is made of an elastic material like rubber. In this case, the input terminal stopper 540 serves as a sealing member for preventing the fluid supplied from the fluid supply device 10 from leaking to the outside through the second input terminal 520 of the connecting unit 500.

Particularly, the formation of the backflow prevention members 521 and 523 of the second input terminal 520 primarily prevents the backflow of the fluid, and the insertion of the surgical instrument like biopsy forceps 20 into the first and second openings 542 and 544 of the input terminal stopper 540 secondarily prevents the backflow of the fluid.

As described above, the fluid supply device 10 for the endoscope 1 according to the present invention can allow the surgeon to easily control the kind of fluid currently supplied, the supply of fluid, and the supply speed, without any surgical assistant's help. Accordingly, manpower waste unnecessary for the endoscopic surgery can be reduced, and the supply of fluid can be performed according to the skill level of the surgeon. Further, the surgeon's foot can be utilized in controlling the supply of fluid to decrease the number of parts controlled by the surgeon's fingers, thereby achieving the endoscopic surgery in more stable and rapid manners.

In addition, the fluid supply device 10 for the endoscope 1 according to the present invention can prevent the fluids supplied to the patient's body from flowing back, thereby avoiding secondary contamination and suppressing disposable products from being unnecessarily used.

Furthermore, the fluid supply device 10 for the endoscope 1 according to the present invention is provided with the bypass unit 600 for removing the liquid remaining in the liquid supply flow path 240 to dry the interior of the liquid supply flow path 240 after the use of the liquid has been finished. Accordingly, there is no need to exchange the liquid supply flow path 240 whenever used, and the fluid supply device 10 can be more sanitarily maintained.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A fluid supply device for an endoscope, comprising:
a gas supply unit for supplying gas to the endoscope;
a liquid supply unit for supplying liquid to the endoscope;
a bypass flow path;
a control unit for controlling operations of the liquid supply unit and the gas supply unit; and
a connector for connecting the liquid supply unit and the gas supply unit to the endoscope and having a first input terminal, a second input terminal, and an output terminal,
wherein
the gas supply unit comprises the following elements serially connected to one another located on a gas supply flow path in order:
a gas tank for storing a gas;
a first opening and closing valve;
a first backflow prevention valve for preventing the supplied gas from flowing back;
a gas pump for supplying gas to the endoscope;
a second opening and closing valve;
a second backflow prevention valve for preventing the supplied gas from flowing back; and
a pressure adjustment valve configured to allow the gas supply flow path to communicate with an atmosphere, thereby preventing an internal pressure of the gas supply flow path from being excessively raised,
the liquid supply unit comprises the following elements serially connected to one another located on a liquid supply flow path in order:
a liquid tank for storing a gas;
a third opening and closing valve;
a third backflow prevention valve for preventing the supplied liquid from flowing back;
a liquid pump for supplying liquid to the endoscope;
a fourth opening and closing valve; and
a fourth backflow prevention valve for preventing the supplied liquid from flowing back,
the bypass flow path is configured to connect the liquid supply flow path and the gas supply flow path, wherein one end of the bypass flow path is connected to a location of the liquid supply flow path located between the third backflow prevention valve and the liquid pump, and the other end of the bypass flow path is connected to a location of the gas supply flow path located between the gas pump and the second opening and closing valve, and
the pressure adjustment valve and the fourth backflow prevention valve are connected to the first input terminal and the second input terminal, respectively.

2. The fluid supply device for an endoscope according to claim 1, further comprising a suction pump located between the third backflow prevention switch and the liquid pump on the liquid supply flow path to suck the gas stored in the gas tank to the liquid supply flow path through the bypass flow path.

3. The fluid supply device for an endoscope according to claim 1, wherein the control unit comprises:
a foot switch located on the floor of an operating room to receive control commands from a surgeon who uses the endoscope; and
a controller for controlling operations of the liquid pump, the gas pump, the first opening and closing valve, the second opening and closing valve, the third opening and closing valve, and the fourth opening and closing valve according to the control commands received.

* * * * *